US008557331B2

(12) United States Patent
Qian et al.

(10) Patent No.: US 8,557,331 B2
(45) Date of Patent: Oct. 15, 2013

(54) ANTIFOULING METHOD AND COMPOSITION USING CHROMEN-4-ONE DERIVATIVES

(75) Inventors: Peiyuan Qian, Hong Kong (CN); Xiaojian Zhou, Hong Kong (CN); Hongping He, Hong Kong (CN); Ying Xu, Hong Kong (CN)

(73) Assignee: The Hong Kong University of Science and Technology, Hong Kong (CN)

( * ) Notice: Subject to any disclaimer, the term of this patent is extended or adjusted under 35 U.S.C. 154(b) by 351 days.

(21) Appl. No.: 12/933,087

(22) PCT Filed: Mar. 20, 2009

(86) PCT No.: PCT/CN2009/070908
§ 371 (c)(1),
(2), (4) Date: Dec. 16, 2010

(87) PCT Pub. No.: WO2009/115051
PCT Pub. Date: Sep. 24, 2009

(65) Prior Publication Data
US 2011/0177237 A1 Jul. 21, 2011

(30) Foreign Application Priority Data
Mar. 20, 2008 (CN) .......................... 2008 1 0087953

(51) Int. Cl.
B05C 13/00 (2006.01)
(52) U.S. Cl.
USPC ....................................................... 427/140

(58) Field of Classification Search
None
See application file for complete search history.

(56) References Cited

FOREIGN PATENT DOCUMENTS

JP 08225409 A * 9/1996

OTHER PUBLICATIONS

Yoshioka et al, Isolation of Flavonoids and Cerebrosides from the Bark of *Prunus jamasakura* as Repellents against the Blue Mussel, *Mytilus edulis*, 1990, Agric. Biol. Chem, 54 (12), p. 3355-3356.*

* cited by examiner

*Primary Examiner* — Dah-Wei Yuan
*Assistant Examiner* — Nga Leung V Law
(74) *Attorney, Agent, or Firm* — Saliwanchik, Lloyd & Eisenschenk

(57) ABSTRACT

A method to utilize a chemical genus of chromen-4-one derivatives as non-toxic, environment friendly antifouling agent, a coating material for objects submerged under the water and subject to biofouling based on the chromen-4-one compounds, as well as a method of obtaining one of such chromen-4-one antifouling compounds, 4',5,7-trihydroxy-isoflavone, from a natural source. Particularly exemplary of such substituted chromen-4-one antifouling compounds are provided and they are 4',5,7 -trihydroxy-isoflavone, 4',5-dihydroxy-3,6,7,8 tetramethoxy-flavone, 3',5-dihydroxy-3,4', 6,8 tetramethoxy-flavone, 4',5-dihydroxy-3,6,7-trimethoxy-flavone, 4',5,7-trihydroxy-flavone, 3',4',6,7-tetrahydroxy-flavone, and 5-monohydroxy-flavone.

9 Claims, 5 Drawing Sheets

SEQUENCE LISTING

```
<160> NUMBER OF SEQ ID NOS: 7

<210> SEQ ID NO 1
<211> LENGTH: 1425
<212> TYPE: DNA
<213> ORGANISM: Streptomyces fungicidicus

<400> SEQUENCE: 1
gtcgaacgat gaaccgcttt cgggcgggga ttagtggcga acgggtgagt aacacgtggg      60
caatctgccc tgcactctgg gacaagccct ggaaacgggg tctaataccg gatatgaccg     120
tctgccgcat ggtggatggt gtaaagctcc ggcggtgcag gatgagcccg cggcctatca     180
gcttgttggt gaggtagtgg ctcaccaagg cgacgacggg tagccggcct gagagggcga     240
ccggccacac tgggactgag acacggccca gactcctacg ggaggcagca gtggggaata     300
ttgcacaatg ggcgaaagcc tgatgcagcg acgccgcgtg agggatgacg gccttcgggt     360
tgtaaacctc tttcagcagg gaagaagcga aagtgacggt acctgcagaa gaagcgccgg     420
ctaactacgt gccagcagcc gcggtaatac gtagggcgca agcgttgtcc ggaattattg     480
ggcgtaaaga gctcgtaggc ggcttgtcac gtcggttgtg aaagcccggg gcttaacccc     540
gggtctgcag tcgatacggg caggctagag ttcgtaggga gatcggaa ttcctggtgt      600 agcggtgaaa tgcgcagata tcaggaggaa caccggtggc gaaggcggat ctctgggccg     660
atactgacgc tgaggagcga aagcgtgggg agcgaacagg attagatacc ctggtagtcc     720
acgccgtaaa cggtgggcac taggtgtggg caacattcca cgttgtccgt gccgcagcta     780
acgcattaag tgccccgcct ggggagtacg gccgcaaggc taaaactcaa aggaattgac     840
gggggcccgc acaagcggcg gagcatgtgg cttaattcga cgcaacgcga agaaccttac     900
caaggcttga catacaccgg aaacgtctgg agacaggcgc cccttgtgg tcggtgtaca     960 ggtggtgcat ggctgtcgtc agctcgtgtc gtgagatggt tgggttaagt cccgcaacga    1020
gcgcaaccct tgtcccgtgt tgccagcagg cccttgtggt gctggggact cacgggagac    1080
cgccggggtc aactcggagg aaggtgggga cgacgtcaag tcatcatgcc ccttatgtct    1140
tgggctgcac acgtgctaca atggccggta caatgagctg cgataccgtg aggtggagcg    1200
aatctcaaaa agccggtctc agttcggatt ggggtctgca actcgacccc atgaagtcgg    1260
agtcgctagt aatcgcagat cagcattgct gcggtgaata cgttcccggg ccttgtacac    1320
accgcccgtc acgtcacgaa agtcggtaac acccgaagcc ggtggcccaa ccccttgtgg    1380
gagggagctt gtcgaaggtg ggactggcga ttgggacgaa gtcgt                    1425

<210> SEQ ID NO 2
<211> LENGTH: 20
<212> TYPE: DNA
<213> ORGANISM: Artificial Sequence
<220> FEATURE:
```

```
<223> OTHER INFORMATION: primer

<400> SEQUENCE: 2
agagtttgat cctggctcag                                              20

<210> SEQ ID NO 3
<211> LENGTH: 19
<212> TYPE: DNA
<213> ORGANISM: Artificial Sequence
<220> FEATURE:
<223> OTHER INFORMATION: primer

<400> SEQUENCE: 3
agagtttgat cctggctca                                               19

<210> SEQ ID NO 4
<211> LENGTH: 18
<212> TYPE: DNA
<213> ORGANISM: Artificial Sequence
<220> FEATURE:
<223> OTHER INFORMATION: primer

<400> SEQUENCE: 4
actcctacgg gaggcagc                                                18

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
cacgagctga cgacagccat                                              20

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
ggytaccttg ttacgactt                                               19

<210> SEQ ID NO 7
<211> LENGTH: 17
<212> TYPE: DNA
<213> ORGANISM: Artificial Sequence
<220> FEATURE:
<223> OTHER INFORMATION: uprimer

<400> SEQUENCE: 7
aaggaggtgw tccarcc                                                 17
```

ANTIFOULING METHOD AND COMPOSITION USING CHROMEN-4-ONE DERIVATIVES

CROSS REFERENCE

This application claims benefit from Chinese patent application number 200810087953.0, filed Mar. 20, 2008, the content of which is hereby incorporated in its entirety by reference.

FIELD OF THE INVENTION

The present invention relates to antifouling methods and materials based on nontoxic bioactive agents. Particularly, it relates to an antifouling method and formulation based on one or more bioactive derivatives of chromen-4-one.

BACKGROUND OF THE INVENTION

Biofouling is the undesirable accumulation of micro-organisms, plants, and animals on artificial surfaces immersed in water such as ship hulls, docks, buoys, etc. More than 4000 organisms having been reported as being species causing biofouling, including bacteria, micro-algae, macro-algae, sea-grass, molluscs, crustacean, etc. Most fouling-causing organisms have a swimming larval stage followed by a sedentary adult stage that remains attached to its substratum throughout the remainder of its life. The attached adult organisms can increase frictional resistance on the hulls of ships, increase the weight of buoys, increase oil flat loading weight, block seawater pipes, decrease water exchange through aquaculture net boxes, and compete for space and food with cultured shellfish, among other negative effects.

The global economic costs due to biofouling are extremely large. For example, biofouling of ships' hulls leads to the high frictional resistance, increase of weight, and subsequent potential speed reduction and loss of maneuverability. As a result, higher fuel consumption is needed, causing increased emissions of harmful compounds. It may also entail a need for heavier and energetically efficient machinery. The estimated economic loss caused by biofouling is around US$ 6 billion annually. The use of a typical antifouling agent (tributyltin) on ship hulls, has saved the US Navy an estimated US$150 million each year. Because of these large-scale economic consequences, development of efficient antifouling methodologies is crucial.

Traditionally, antifouling materials are metal based. Prior to the 17th century, plumbum was the most common antifouling agent. From 1960's until recently, organotins, represented by tributyltin (TBT), were common anti-fouling agents. However, environmental concerns over the effect of organotins first arose in France, where severe problems were encountered in commercial oyster fisheries in areas where there was intense boating activity and poor tidal exchange. Since then, the distribution, fate and effects of organotins and other antifoulants on the marine and freshwater environment have been under intense scrutiny. Research suggests damaging effects of organotins on reproduction and growth of various marine life. In addition, TBT is known to threaten non-target organisms in the marine ecosystem, causing dramatic effects on shell fishes by inducing imposex in large populations. At concentrations as low as 1 ng/L, TBT can induce imposex. Now, TBT is regarded as one of the most toxic and hazardous compounds introduced into marine environments. In response to these concerns, the Marine Environment Protection Committee (MEPC) of the International Maritime Organization (IMO) has implemented a ban on the application of TBT paints from 1 Jan. 2003, with the intent that no TBT paints will remain on vessels after 1 Jan. 2008.

As an alternative, vessels are increasingly painted with copper-based paints. However, copper-based paints also have negative effects on the marine environment. For example, oysters accumulate considerable amounts of copper and copper is toxic to marine algae.

The toxicity concern is not only on TBT, but on all anti-fouling biocides, and has thus stimulated research and development of non-toxic antifouling coatings. The development of a marine paint or paint ingredient that is non-toxic, non-heavy-metal-based, and benign to the marine environment is urgently sought. The present invention provides a number of environmentally-friendly, natural anti-fouling agents, compositions, and applications.

SUMMARY OF THE INVENTION

One object of the present invention is to provide a chemical genus from which the compound is likely nontoxic but has potent antifouling activities. Another object of the present invention is a method of obtaining such chemical compound from marine micro-organisms.

This and other objects of the present invention are realized by providing a group of substituted chromen-4-one derivatives, which show a potent antifouling activity but are non-toxic and environmental friendly. As used in this invention, the term "substituted chromen-4-one antifouling compound" means a species of a substituted chromen-4-one genus, which has at least one substituent on each of the two rings (i.e., the benzene ring and pyran ring) of chromen-4-one, of which the backbone is represented by formula I. The substituent on the pyran ring comprises an aromatic ring, preferably a benzene ring, and the substituent on the benzene ring is preferably a hydroxy (OH) or methoxy ($CH_3O$) group.

I

Preferable antifouling chromen-4-one derivatives according to the present invention have: (a) an aromatic ring, preferably a benzene or substituted benzene group, attached at position 2 or position 3, preferably at position 2, (b) has a hydroxyl at position 5, and (c) has no bulky substituent group (such as monosaccharide or amylose) attached at position 3 (preferably absence of any substituent) when there is a substituent at position 2. For example, following this guideline, the following substituted chromen-4-one compounds of formula II are particular embodiments of the present invention:

wherein $R_5$, $R_6$, $R_7$, $R_8$ are independently H, OH, or $OCH_3$; and $R_2$, $R_3$, are independently H, $OCH_3$, Ph, or substituted Ph, provided that when $R_2$ is Ph or substituted Ph, $R_3$ is H or $OCH_3$ and when $R_3$ is Ph or substituted Ph, $R_2$ is H or $OCH_3$. Examples of substituted Ph are:

The chemical genus of chromen-4-one derivatives of the present invention is mostly known but it is unknown that any species in this genus has any antifouling effect. In addition, the present invention also provides a previously unknown source or method of obtaining this compound. It is from a natural source, i.e., a marine species *Streptomyces fungicidicus*. The compound genus of the prevent invention is advantageous for two reasons. First, marine micro-organisms represent a sustainable source to tackle the current biofouling problems and fermentation requires less manpower and is more environmentally and economically friendly. Second, there are many commercially available derivative compounds in this genus, permitting effective structure-activity relationship analyses. Such analyses can lead to more effective derivative compounds which are more suitable for semi or total chemical synthesis and thus can be produced more economically on an industrial scale. Moreover, being derived from naturally occurring compounds, all the antifouling compounds of the present invention, are heavy-metal free, and very likely nontoxic and decomposable in marine environments.

As particular non-limiting embodiments of the present invention, the following seven (7) compounds are representatives of the chromen-4-one genus of the present invention as a guideline for the scope that the present invention pertains:

Compound 1: 4',5,7-trihydroxy-isoflavone (genistein)

Compound 2: 4',5-dihydroxy-3,6,7,8 tetramethoxy-flavone (calycopterin)

Compound 3: 3',5-dihydroxy-3,4',6,8 tetramethoxy-flavone (casticin)

Compound 4: 4',5,-dihydroxy-3,6,7-trimethoxy-flavone (penduletin)

Compound 5: 4',5,7-trihydroxy-flavone (apigenin)

Compound 6: 3',4',6,7-tetrahydroxy-flavone (luteolin)

Compound 7: 5-monohydroxy-flavone (primuletin)

The seven (7) antifouling compounds as particular embodiments of the present invention, are all within the above defined chemical genus and obtained by the bioassay guided isolation from metabolites of marine micro-organism, or from terrestrial plants by the bioassay confirmed structure-activity relationship analysis. The results of experiments have proved that all the natural compounds in the present invention are nontoxic and promising antifouling compounds. The antifouling paints based thereon are also environmentally safe.

A further object of the present invention is to provide a cultivation method for producing manufacture chromen-4-one derivatives. As a particular embodiment, a cultivation method is described herewith in detail, which is used to produce 4',5,7-trihydroxy-isoflavone from the marine fungus Streptomyces fungicidicus. Without undue experimentation, people having ordinary skill in the art may apply or modify the method described herein for 4',5,7-trihydroxy-isoflavone in practicing other antifouling chromen-4-one derivatives of the present invention, which may be isolated from natural sources or chemically synthesized and commercially available.

The foregoing objects of the present invention are in one inventive unit, united by a novel technical feature, that is, the antifouling effect of the substituted chromen-4-one compounds.

The various features of novelty which characterize the invention are pointed out with particularity in the claims annexed to and forming a part of this disclosure. For a better understanding of the invention, its operating advantages, and specific objects attained by its use, reference should be made to the drawings and the following description in which there are illustrated and described preferred embodiments of the invention.

DETAILED DESCRIPTION OF PARTICULAR EMBODIMENTS OF THE INVENTION

A. The Strains Producing Antifouling Compounds

The strain of Streptomyces fungicidicus was isolated from sediment samples from 5000 m depth in west Pacific Ocean (N10°50'35"; W154°05'28"). The samples were kept at 0° C. and 44° C. before and after arriving laboratory, respectively.

The strain of S. fungicidicus was isolated by the following enrichment techniques. Sediment samples (about 1 g) were suspended in 10 ml artificial seawater. After mixing, 200 μl of the suspension was spread on 2216E agar plate and incubated at 10° C. Colonies with different shape or color were transferred to a new agar plate for new incubation and further isolation. The final identification was conducted by detection of 16S rRNA sequence (SEQ ID No: 1). 16S rRNA sequence was amplified by the primers 8F (5'-AGAGTTTGATCCTG-GCTCAG-3') and 1525R (5'-AGAGTTTGATC CTG-GCTCA-3'). Sequencing reactions were performed by using forward primers 26F (5'-AGAGTTTGATC CTGGCTCA-3') and 355F (5'-A CTCCTACGGGAGGCAGC-3') and reverse primers 1492R (5'-GGYTACCTTGTTACGAC TT-3') and 1525R (5'-AAGGAG GTGWTCCARCC-3'), SEQ ID Nos: 2-7, respectively. The sequence was deposited in Genbank under accession NO. AY636155.

The sequence was analyzed for similarity with other known sequences with BLAST program (National Center for Biotechnology Information (NCBI). BLAST results showed that the strain is Streptomyces fungicidicus strain YH04 (Accession no. AY636155, identity=99%).

Figure 1:
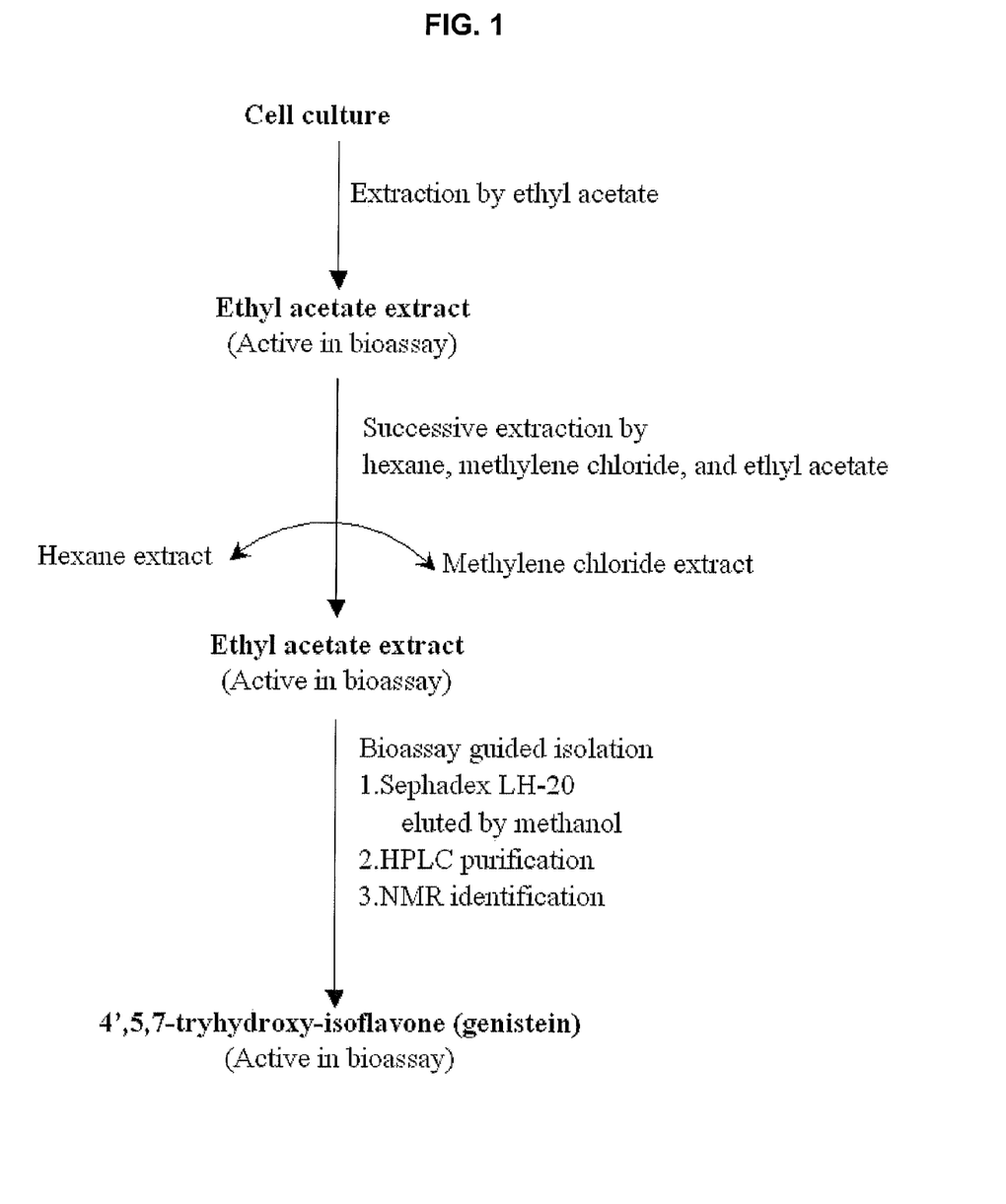
FIG. 1 is a flowchart of the bioassay-guided isolation of 4',5,7-tryhydroxy-isoflavone (genistein) from the culture of Streptomyces fungicidicus.

B. Isolation and Identification of Antifouling Compound from Marine Micro-Organism A Streptomyces fungicidicus strain was inoculated into culture media of pH 7.8 containing 20 g malt extract, 8 g Yeast extract, 8 g glucose, and 1.5 L filtered seawater. About 60 L cell suspensions were collected after the strain was incubated for 10 days by 110 rpm shaking. Cells were separated from fermentation broth by centrifugation and both subjected to triplicate ethyl acetate extractions separately. About 8 g black oil was obtained after collecting all extraction and volatilization of solvent, and was subjected to the isolation and identification as described in FIG. 1.

The structure of this compound was identified by NMR (1HNMR, 13CNMR, DEPT and COSY). The molecular weight of the compound was determined by negative ESI-MS (Waters Micromass ZQ ESI-MS). ESI-MS: [M-H]-m/z 269. The detailed data for 1H NMR and 13C NMR spectra are listed as following. 1H NMR (400 MHz, DMSO-d6) δ: 12.97 (C5-OH), 10.91 (C4'-OH), 9.61 (C7-OH), 8.33 (s, 1H, H-2), 7.38 (2H, d, J=8.5 Hz, H-2',6'), 6.82 (2H, d, J=8.5 Hz, H-3',5'), 6.39 (s, 1H, H-8), 6.23 (s, 1H, H-6). 13C NMR (100 MHz, DMSO-d6) δ: 93.5 (C-8), 98.8 (C-6), 104.3 (C-10), 114.9 (C-3', 5'), 121.0 (C-3), 122.1 (C-1'), 130.0 (C-2', 6'), 153.9 (C-2), 157.3 (C-9), 157.4 (C-5), 161.8 (C-4'), 164.1 (C-7), 180.1 (C-4).

Based on above data, the compound was identified as: 4',5,7-tryhydroxy-isoflavone (genistein):

Other compounds can be made according to publicly known methods and/or from commercial sources. For example, compound 2 can be prepared according to T. R. Seshadri and V. Venkateswarlu. A synthesis of calycopterin. Proceedings of the Indian Academy of Sciences, Section A. Volume 24, 1946, Pages 349-351, and compound 4 can be synthesized according to S. E. Flores, J. Herrin and H. Menchaca. The synthesis of penduletin. Tetrahedron. Volume 4, Issues 1-2, 1958, Pages 132-134. Compounds 1, 5, 6, and 7 can be bought from Sigma-Aldrich (6000 North Teutonia Avenue, Milwaukee, Wis. 53209, Phone: 1-800-231-8327). The commercial products are detailed as follows:

Compound 1
Name: Genistein; IUPAC: 5,7-dihydroxy-3-(4-hydroxyphenyl)-4H-chromen-4-one; MF: C15H10O5; CAS #: 446-72-0; and Prod. # G6649, G6776.

Compound 5
Name: Apigenin; IUPAC: 5,7-dihydroxy-2-(4-hydroxyphenyl)-4H-chromen-4-one; MF: C15H10O5; CAS #: 520-36-5; and Prod. # A3145, 10798.

Compound 6
Name: Luteolin; IUPAC: 2-(3,4-dihydroxyphenyl)-5,7-dihydroxy-4H-chromen-4-one; MF: C15H10O6; CAS #: 491-70-3; and Prod. # L9283.

Compound 7
Name: 5-Hydroxyflavone; IUPAC: 5-hydroxy-2-phenyl-4H-chromen-4-one; MF: C15H10O3; CAS #: 491-78-1; and Prod. # H4405.

Compounds 3 can be obtained from Chengdu Biopurify Phytochemicals Ltd. (Address: 2F, No. 11 Building, No. 388 Rongtaidadao CNSTP, Wenjiang Zone, Chengdu, Sichuan, China, 611130, Tel: +86-28-66780410, Fax: +86-28-82633165). The commercial product is: Name: Casticin (Vitexicarpin); IUPAC: 3',5-Dihydroxy-3,4',6,7-tetramethoxy-flavone; MF: C19H18O8; CAS #: 479-91-4; and Prod. # C07067.

C. Bioassay for Antifouling Activity of Genistein Against Larval Settlement

Larvae were obtained from the adult barnacles B. amphitrite collected from the intertidal zone in Hong Kong (22°19'N, 114°16'E). The larvae were reared in freshly filtered natural seawater (FSW, 0.45 μm, 32S salinity) and fed with Chaetoceros gracilis Schutt at 24° C. in the Coastal Marine Laboratory, the Hong Kong University of Science and Technology (HKUST). Larvae that were competent to settle (called cyprids) were stored for 2 days at 8° C. prior to being used in the bioassays. Ten μl of each test sample dissolved in dimethyl sulfoxide (DMSO) were transferred into a well in 24-well polystyrene plate after the addition of 1 ml of FSW. The control wells contained 1 ml of FSW and 10 μl of DMSO. About 15 cyprids were added in each well with triplicate samples being tested. The numbers of settled juveniles, dead larvae, or moving larvae in each well were counted after 24 h of incubations at 24° C. in the dark to calculate EC50 or LC50.

Figure 2:
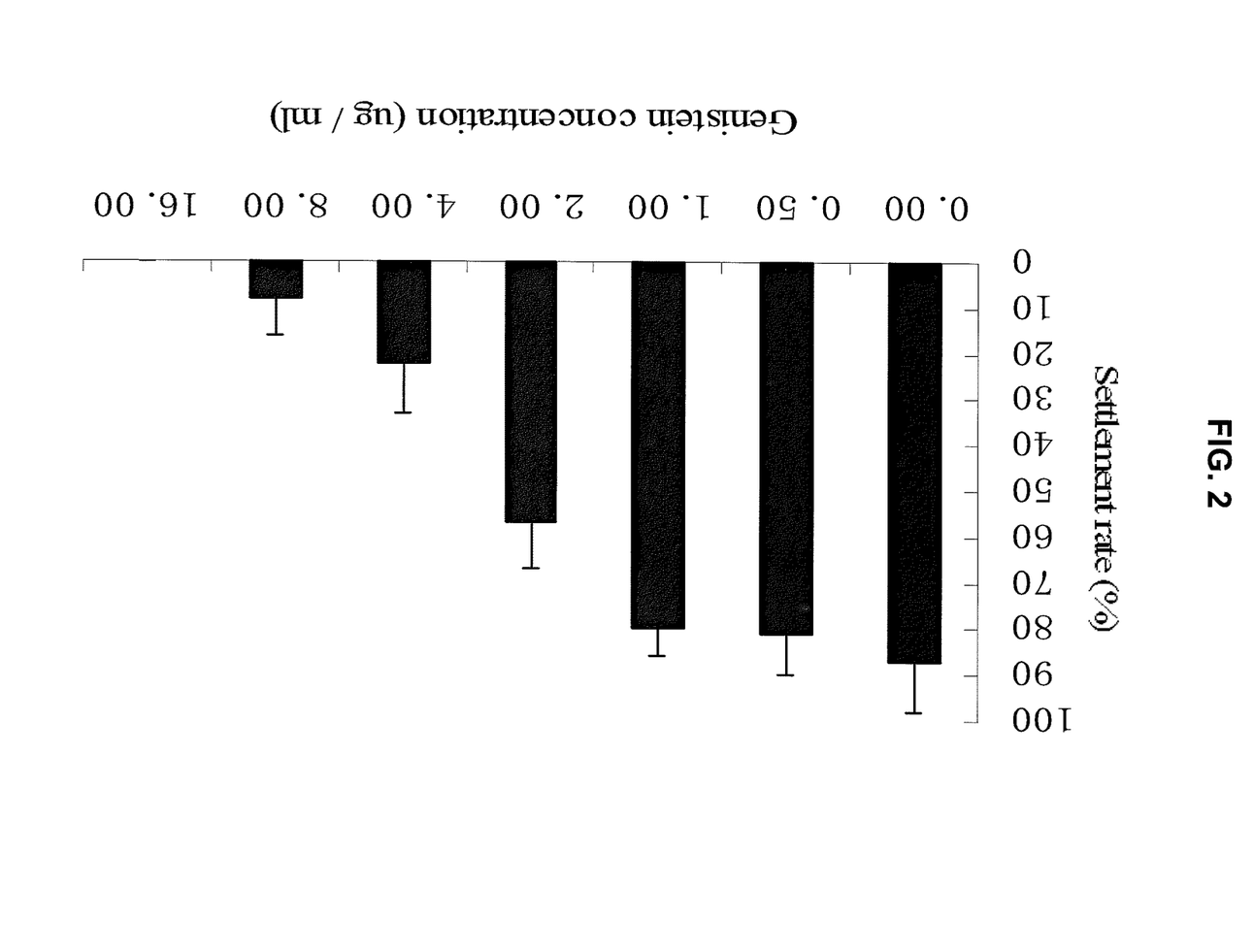
FIG. 2 shows the inhibitory effect of the compound 4',5,7-tryhydroxy-isoflavone (genistein) on larval settlement of the barnacle Balanus amphitrite. The results are presented as the mean±standard deviation of at least three replicates (n=3).

As shown in FIG. 2, the inhibitory activity of genistein against larvae settlement was observed at a concentration as low as 0.5 μg/ml. In the concentration of 8 μg/ml, 10% of the larvae settled, which is significantly less than in the control (90% settlement). According to the method of Rittschof et al. (1994), the EC50, LC50 and LC50/EC50 values of genistein were measured as 3.0 μg/ml, >50 μg/ml, and >16.7, respectively. The results indicate the present compound are nontoxic since its LC50/EC50 value is higher than 10 (Avelin et al. 1993), while LC50/EC50 values for toxic heavy metal is around 1.

D. Hydrolysis Experiment of Genistein

The experiments were carried out according to the method described in ASTM (1993). Buffer solutions consisting of 20 mM of sodium acetate were prepared with adjusted pH level at 5, 7, and 9. FSW was the same as those used in bioassays. Artificial seawater (ASW) was prepared as van't Hoff formula (460 mM NaCl, 10.1 mM KCl, 9.2 mM $CaCl_2$, 35.9 mM $MgCl_2$, 17.5 mM $MgSO_4$, 10 mM Tris-HCl, and pH 8.2). Test solution (900 ml) containing 4 μg genistein was divided into nine test glass tubes (100 ml each), and then the tubes were tightly capped. Immediately after preparation of the test solutions, three tubes were loaded onto a Sep-Pak tC18 ENV column (Waters, USA), preconditioned for use by eluting it with methanol and water under reduced pressure. The column after loading the test sample was eluted with water to remove any salts in the test samples, and was then eluted with 2.5 ml of DMSO. Thus, the eluate was 40 times more concentrated than the sample in the original test solution; this concentrated solution was subjected to HPLC analysis. The HPLC system (600, Waters, USA) was equipped with a photodiode array detector (996, Waters, USA) installed in tandem after outlet of the column (Phenomenex Luna 5λ C18 100A, 250×4.60 mm, 5 micron). The solvents used were (A) 5% acetonitrile and (B) 95% acetonitrile at the isocratic flow rates of (A) 0.53 ml $min^{-1}$ and (B) 0.47 ml $min^{-1}$ at 40° C., respectively. A volume of ten μl of elute was injected into the column using an autosampler (717plus, Waters, USA). The UV absorption at 1=260 nm was used for quantification. The analytical data were shown as the average value of triplicate analyses. The remaining six tubes were kept at 50° C. in the dark in an incubator for a period of four or seven days according to ASTM Procedure E895-89 (ASTM, 1993). After the incubations, each of three test samples was subjected to HPLC analysis, following the same concentration process as described above to determine the remaining concentration of genistein.

Figure 3:
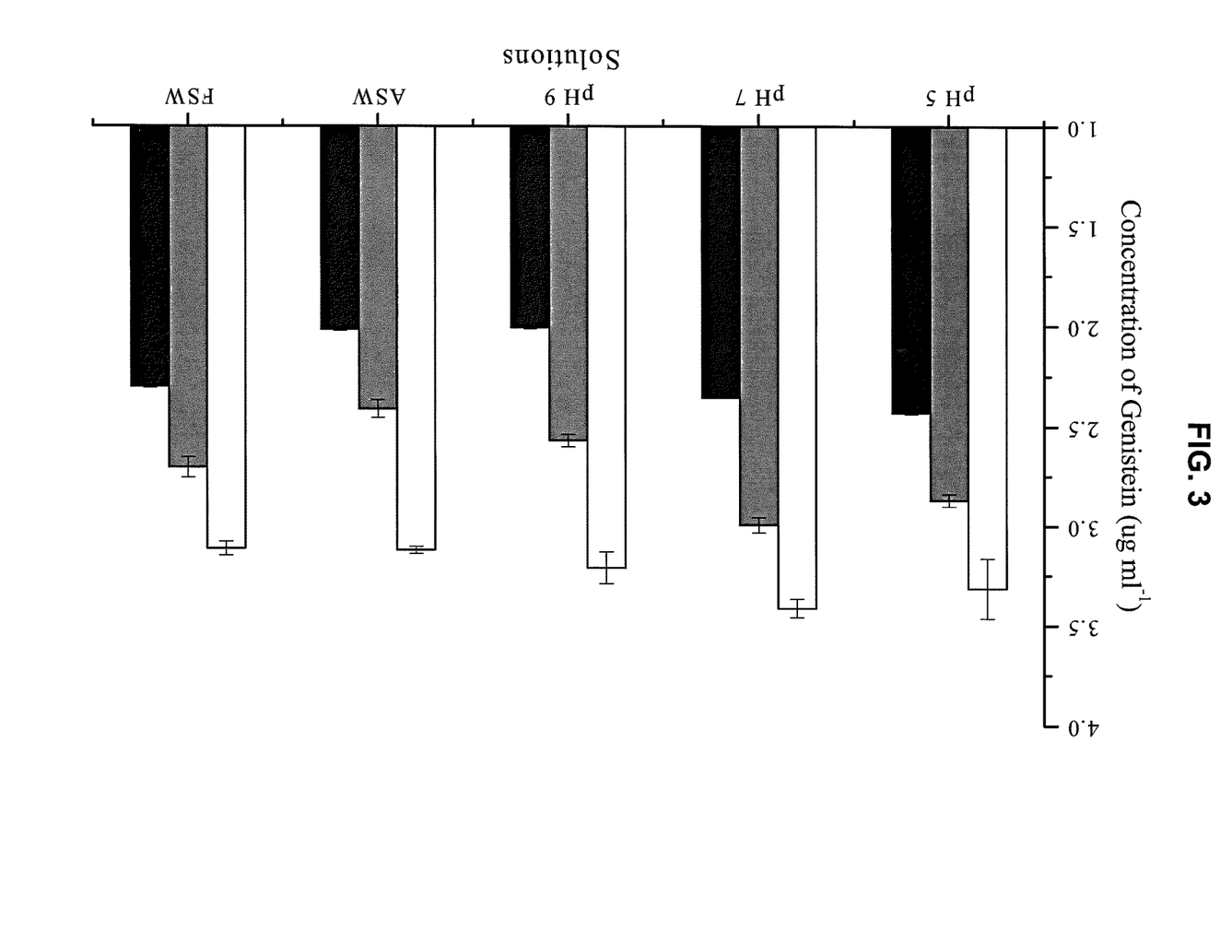
FIG. 3 shows hydrolysis of genistein in buffer solutions, artificial seawater and natural seawater. The concentrations were determined by HPLC before hydrolysis (open bar), after 4 days (gray bar), and 7 days (black bar) of incubation at 50° C. in dark for hydrolysis. Tested solutions included artificial seawater (ASW), filtered natural seawater (FSW), and 20 mM acetic buffers of pH 5, 7, and 9. The concentration of genistein was presented as the mean±standard deviation of three replicates (n=3).

As shown in FIG. 3, the concentration of genistein significantly reduced after being stored in 50° C. for a week. About 27, 31, 37, 35, and 26% of genistein were decomposed in pH 5.0, 7.0, and 9.0 buffer solutions, ASW, and FSW, respectively. These results indicate that genistein can be decomposed in marine environments and the accumulation of genistein would not seriously occur in marine environments.

E. Field Experiment of Genistein

Test compounds (genistein, $Cu_2O$, or their mixture) were mixed with resin-based paint (Permoglaze, Akzo Nobel Decorative Coatings, Lancashire, UK) with addition of 15% of (w/w) xylene, and then sprayed on the surface of PVC panels (size: 10 cm×10 cm×0.5 cm). Genistein was incorporated into paint by 10 and 20% of the dry weight as the low and high concentrations, respectively. In the experiments of combination effects, both $Cu_2O$ and genistein at 10% of dry weight were added. The controls used was a resin based paint with addition of 15% (w/w) of xylene only. Each of the tested paints was mixed for more than 8 h before being spread onto panels. The thickness of each paint film was between 100 and 150 μm. The painted panels were air-dried completely prior to being tied to PVC frames and deployed vertically at a depth of 1-1.5 m at the pier of HKUST from March to June in 2007. The numbers of adult barnacle *B. amphitrite* on the surface were counted and the density on each panel was calculated after their submergences. Four replicates were tested for each sample. As shown in Table 1, the statistical analysis clearly showed that the presence of genistein on the painted panel surfaces significantly reduced barnacle fouling (Student's T-test: $p<0.05$). The statistical analysis demonstrated the clear difference between the single and mixed compounds even after three months of submergence (Student's T-test: $p<0.01$). The mixture achieved much better antifouling performance than single compound, indicating that genistein has the potential to be used as mixture with other antifoulants.

TABLE 1

The density of barnacles fouled on the test panels. The content of compounds was the percentage of the compound weight per dried weight of paint. Control paint did not contain $Cu_2O$ or genistein. The densities (adults $cm^{-2}$) of the barnacle *Balanus amphitrite* on the surfaces of panels were denoted as the mean ± standard deviation of four replicate panels. The statistical differences (n = 4) between the controls and the treatments, and between single $Cu_2O$, genistein, and their mixture were calculated using Student's paired t-test and indicated at the significance level of: * = $p < 0.05$ and ** = $p < 0.01$.

| Submergence | Control | 10% genistein | 20% genistein |
|---|---|---|---|
| One month | 0.32 ± 0.039 | 0.12 ± 0.031 ** | 0.08 ± 0.027 ** |
| Two months | 0.71 ± 0.053 | 0.57 ± 0.055 * | 0.13 ± 0.029 ** |

| | 10% $Cu_2O$ | 10% genistein | 10% $Cu_2O$ + 10% genistein |
|---|---|---|---|
| Three months | 0.81 ± 0.06 ** | 0.77 ± 0.042 ** | 0.39 ± 0.053 |

F. Screening for Bioactive Chromen-4-One Derivatives

Larvae were obtained from the adult barnacles *B. amphitrite* collected from the intertidal zone in Hong Kong (22°19'N, 114°16'E). The larvae were reared in freshly filtered nature seawater (FSW, 0.45 μm, 32S salinity) and fed with *Chaetoceros gracilis* Schutt at 24° C. in the Coastal Marine Laboratory, the Hong Kong University of Science and Technology (HKUST). Cyprids (competent larvae) were stored for 2 days at 8° C. (aged cyprids) prior to being used in the bioassays. Ten μl of each test sample dissolved in dimethyl sulfoxide (DMSO) were transferred into a well in 24-well polystyrene plate after the addition of 1 ml of FSW. The control wells contained 1 ml of FSW and 10 μl of DMSO. About 15 cyprids were added in each well with triplicate samples being tested. The numbers of settled juveniles, dead or the moving larvae in each well were counted after 24 h of incubations at 24° C. in the dark to calculate EC50 or LC50.

Figure 5:
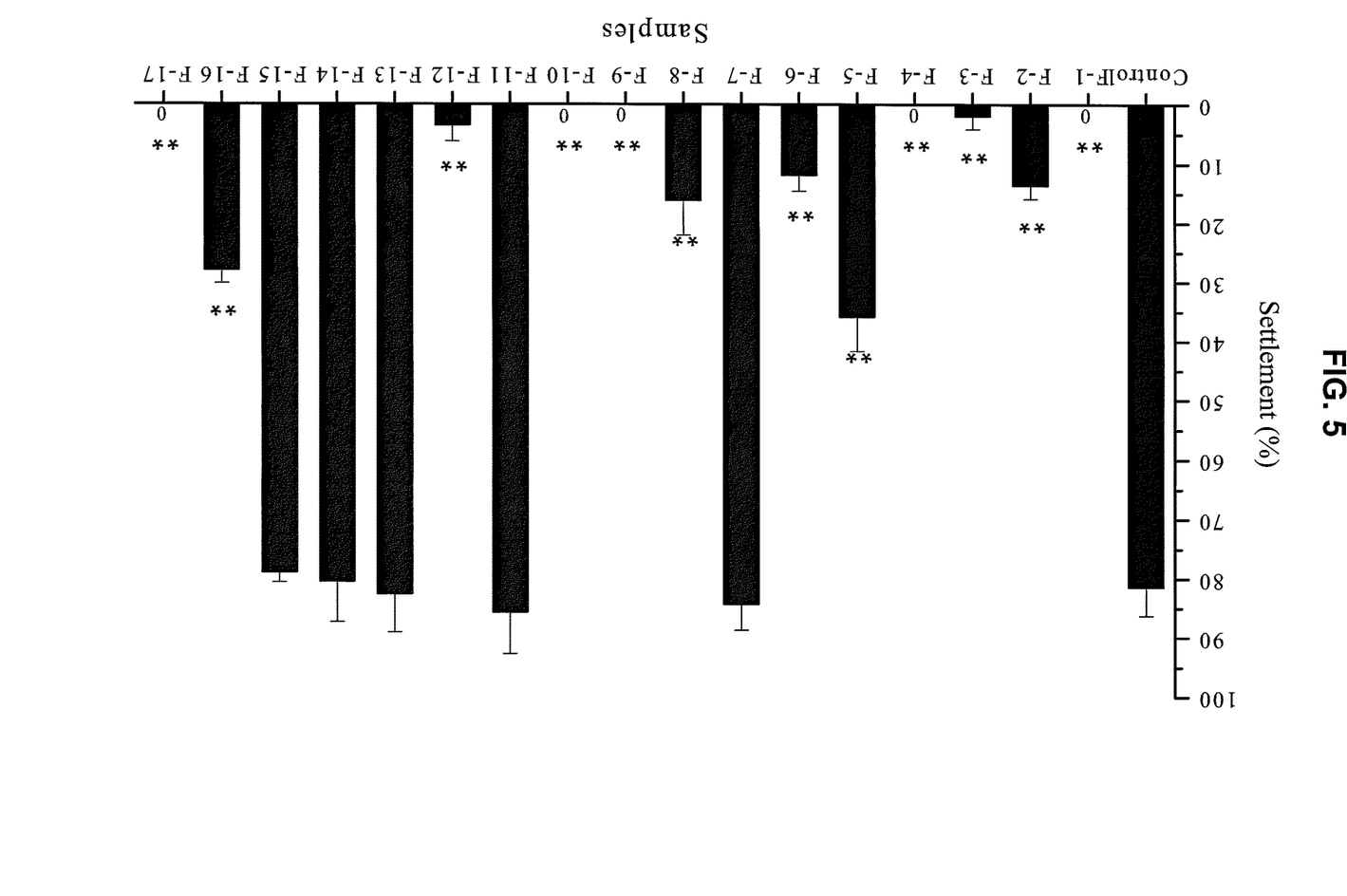
FIG. 5 shows the inhibitory effect of the tested samples on larval settlement (%) of the barnacle Balanus amphitrite. The concentration of each sample was at 50 μg ml$^{-1}$. The results are presented as the mean±standard deviation of at least four replicates (n=4). The statistical differences between the controls and the samples were calculated using Student's paired t-test and indicated at the significance level of: *=p<0.05 and **=p<0.01 on the top of each bar.

As shown in FIG. 5, 12 among 17 kinds of chromen-4-one derivatives had a significant antifouling activity against larval settlement (**: Student's paired t-test: $p<0.01$). The antifouling activity was determined according to the method of Rittschof et al. (1994).

In Table 2, genistein was purified from extract of *Genista tinctoria*, a plant species. It was also shown to have the antifouling activity with EC50=3.0 ug/ml and LC50/EC50>16.7, which is exactly the same as that from marine bacteria *Streptomyces fungicidicus*. The above data also demonstrate that genistein is a nontoxic antifouling compound according to the standard of Avelin et al. (1993) since its LC50/EC50 was detected as >16.7.

TABLE 2

The EC50 and LC50/EC50 ratio of potential antifoulants against larval settlement of the barnacle *Balanus amphitrite*. For each compound, the EC50 value presented here is mean ± standard deviation of at least three replicates; the LC50 value used for calculation of LC50/EC50 is the highest concentrations causing <50% death of larvae. The other 5 flavone and isoflavone derivatives EC50 with larger than 50 μg $ml^{-1}$ were not included.

| Samples | Chemical name | $EC_{50}$ | $LC_{50}/EC_{50}$ |
|---|---|---|---|
| F-1 | calycopterin | 3.4 ± 0.5 | >14.7 |
| F-2 | 7-hydroxy-8,4'-dimethoxyisoflavone | 13.3 ± 2.5 | >7.50 |
| F-3 | casticin | 3.0 ± 0.4 | >16.7 |
| F-4 | 5,4'-dihydroxy-3,6,7-trimethoxyflavone | 2.5 ± 0.3 | >20.0 |
| F-5 | neoisorutin | 40.1 ± 3.4 | >5.0 |
| F-6 | kaempferol | 9.6 ± 1.4 | >5.2 |
| F-8 | 3,5-dihydroxy-7,4'-dimethoxyflavone | 11.8 ± 2.1 | >4.2 |
| F-9 | apigenin | 3.1 ± 0.3 | >16.1 |
| F-10 | luteolin | 3.8 ± 0.4 | >13.2 |
| F-12 | genistein | 3.0 ± 0.3 | >16.7 |
| F-16 | icariin | 35.3 ± 4.2 | >2.8 |
| F-17 | primuletin | 2.8 ± 0.3 | >17.9 |

Figure 4:
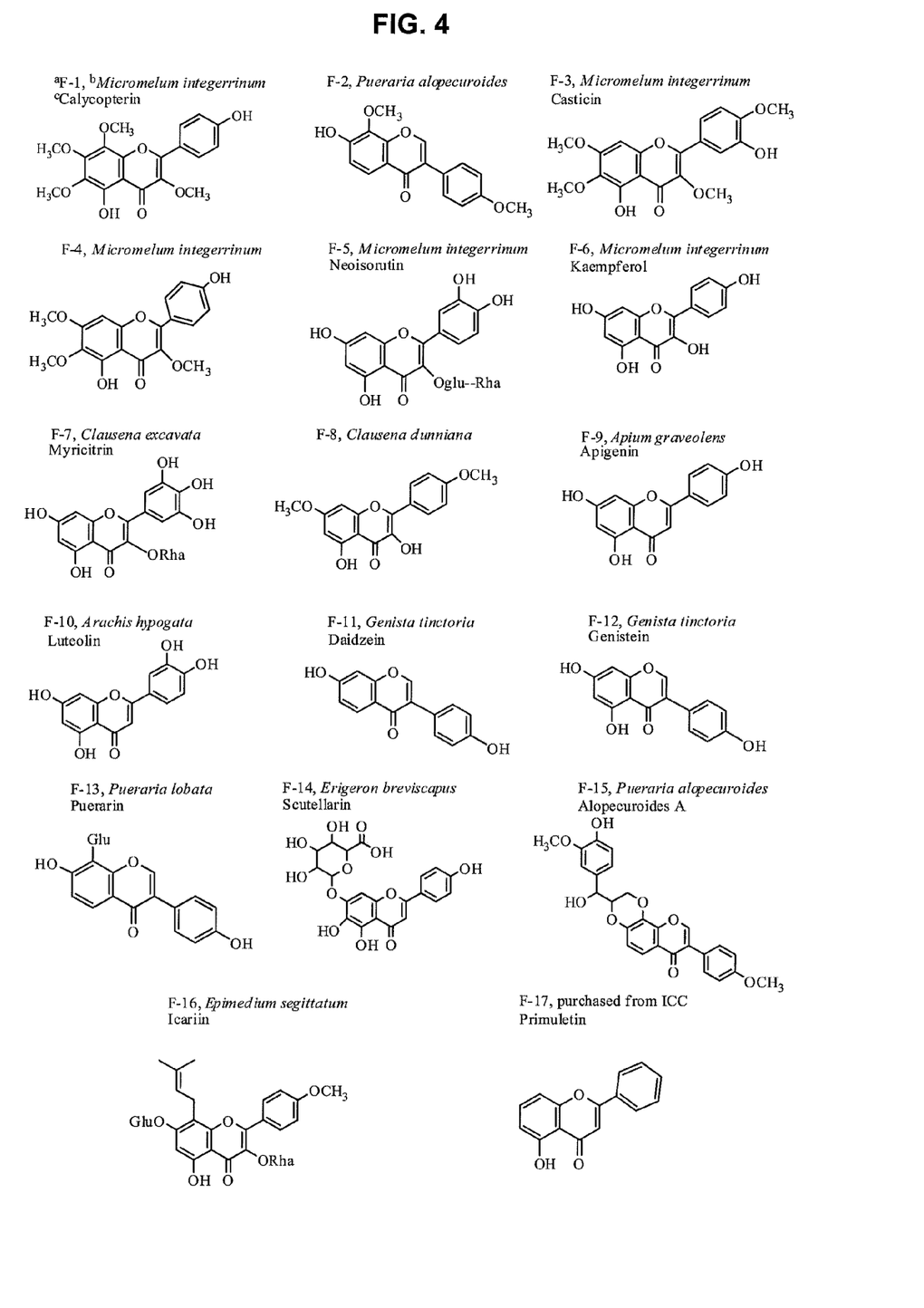
FIG. 4 shows molecular structures and source plants of chromen-4-one derivatives tested. The text above each structure of the compound indicates (a) the sample number, (b) the source plant, and (c) the popular name for the compound, if available.

As shown in Table 2 and FIG. 5, six out of the 12 chromen-4-one derivatives showed almost no toxicity but have the similar antifouling activity as genistein with EC50 around 3.0 ug/ml. These 6 compounds are 3',5-dihydroxyl-3,6,7,8-tetramethoxy-flavone (F-1, calycopterin), 3',5-dihydroxyl-3,4',6,7-tetramethoxy-flavone (F-3, casticin), 4',5-dihydroxy-3,6,7-trimethoxy-flavone (F-4), 4',5,7-trihydroxy-flavone (F-9, apigenin), 3',4',5,7-tetramethoxy-flavone (F-10, luteolin), and 5-monohydroxyl-flavone (F-17, primuletin). The structure and source of the compounds are shown in FIG. 4.

The above 7 compounds can be utilized as examples of environmentally-friendly antifoulants, which also can be chemically modified to achieve high activities or to reduce cost. Using only ordinary skill in the art, other substituted chromen-4-one antifouling compounds can be made by adding or removing one or more substituent groups, according to the following guideline:

There should be at least one substituent on each of the two rings (i.e., the benzene ring and pyran ring) of chromen-4-one. The substituent on the pyran ring should be a substituted or unsubstituted aromatic ring group. Up to 4 substituents can be attached to the benzene ring of chromen-4-one and should first consider a hydroxy (OH) or methoxy ($CH_3O$) group as candidates for substituents at the benzene ring before consider other type of suitable substituent groups. If there is substituent attached at position 2 of the pyran ring, then it should be considered to leave position 2 of the pyran ring unsubstituted or substituted with a less bulky group.

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

What is claimed is:

1. A method of preventing, inhibiting, or reducing biofouling on a surface of an object submerged in water, wherein the method comprises applying a coating material to a surface of an object submerged, or to be submerged, in water, wherein said coating material comprises at least one substituted chromen-4-one antifouling compound and a carrier;

wherein said substituted chromen-4-one antifouling compound has the following formula:

wherein $R_5$, $R_6$, $R_7$, $R_8$ are independently H, OH, or $OCH_3$;
$R_2$ is H or $OCH_3$; and
$R_3$ is Ph or a substituted Ph selected from the group consisting of:

, and

2. The method of claim 1, wherein $R_3$ is Ph.
3. The method of claim 1, wherein $R_3$ is 4. The method of claim 1, wherein $R_3$ is 5. The method of claim 1, wherein $R_3$ is 6. The method of claim 1, wherein $R_5$ is OH.
7. The method of claim 1, wherein $R_6$ is OH or $OCH_3$.
8. The method of claim 1, wherein $R_7$ is H or $OCH_3$.
9. The method of claim 1, wherein $R_8$ is OH or $OCH_3$.

* * * * *